US006384077B1

(12) United States Patent
Peet et al.

(10) Patent No.: US 6,384,077 B1
(45) Date of Patent: May 7, 2002

(54) HIGHLY PURIFIED EPA FOR TREATMENT OF SCHIZOPHRENIA AND RELATED DISORDERS

(75) Inventors: Malcolm Peet, Sheffield (GB); Krishna S Vaddadi, Melbourne (AU)

(73) Assignee: Laxdale Limited, Stirling (GB)

( * ) Notice: Subject to any disclaimer, the term of this patent is extended or adjusted under 35 U.S.C. 154(b) by 0 days.

(21) Appl. No.: 09/492,741

(22) Filed: Jan. 27, 2000

(30) Foreign Application Priority Data

Jan. 27, 1999 (GB) .............................................. 9901809

(51) Int. Cl.$^7$ .............................................. A61K 31/20
(52) U.S. Cl. ...................................................... 514/560
(58) Field of Search ......................................... 514/560

(56) References Cited

U.S. PATENT DOCUMENTS

| 5,252,333 A | 10/1993 | Horrobin ..................... 424/422 |
| 5,840,944 A | 11/1998 | Furihata et al. ............. 554/175 |

FOREIGN PATENT DOCUMENTS

| GB | 2148713 A | 6/1985 |
| WO | WO98/16216 | 4/1998 |

OTHER PUBLICATIONS

Malcolm Peet et al, Phospholipid Spectrum Disorder in Psychiatry pp. 1–19, 1999.
Brian E. Leonard, Fundamentals of Psychopharmacology, pp. 186–187, 1997.
Diagnostic and Statistical Manual of Mental Disorders, 4$^{th}$ Ed., published by the American Psychiatric Assoc., pp. 285, 1995.
Martin A. Samuels, M. D. et al, Office Practice of Neurology, Chapter 122, Huntington's Disease, pp. 654–655, 1996.
S. Leucht et al, Schizophrenia Research, vol. 35, "Efficacy and extrapyramidal side–effects . . .", pp. 51–68, 1999.
Nina Willumsen et al, Biochimica et Biophysica Acta. vol. 1369, "On the effect of 2–deuterium–. . . ", pp. 193–203, 1998.

E. Mayatepek et al, The Lancet, vol. 352, "Leukotriene C4–synthesis deficiency . . . ", pp. 1514–1517, Nov. 7, 1998.
Atsushi Yamashita et al, J. Biochem., vol. 122, No. 1, "Acyl–transferases and Transacylases . . . ", pp. 1–16, 1997.
Yang Cao et al, Genomics, vol. 49, "Cloning, Expression, and Chromosomal Locatlization . . . ", pp. 327–331, 1998.
Monica Piccini et al, Genomics, vol. 47, "FACL4, a New Gene Encoding Long–Chain Acyl–CoA . . . ", pp. 350–358, 1998.
Michael J. Finnen et al, Biochemical Society Trans., "Purification and characterisation . . . ", pp. 19, 1991.
Andrew L. Stoll et al, Arch. Gen. Psychiatry, vol. 56, "Omega 3 Fatty Acids in Bipolar Disorder", pp. 407–412, May 1999.
B. Puri et al, Archives of General Psychiatry, No. 55, "Sustained remission of positive and . . . ", pp. 188–189, 1998.
Stephen T. Warren, Science, vol. 271, "The Expanding World of Trinucleotide Repeats", pp. 1374–1375, Mar. 8, 1996.
Victor O. Ona et al, NATURE, vol. 399, "Inhibition of caspase–1 slows disease progression . . . ", pp. 263–267, May 20, 1999.
Philippe Dijan et al, Proc. Natl. Acad. Sci., vol. 93, "Codon repeats in genes associated . . . ", pp. 417–421, Jan. 1996.
M. Flint Beal, MD, Annals of Neurology, vol. 38, No. 3, "Aging, Energy, and Oxidative Stress in . . . ", pp. 357–366, Sep. 1995.

*Primary Examiner*—William R. A. Jarvis
(74) *Attorney, Agent, or Firm*—Jacobson Holman, PLLC

(57) ABSTRACT

A pharmaceutical preparation comprising EPA in an appropriately assimilable form where of all the fatty acids present in the preparation at least 90%, and preferably at least 95%, is in the form of EPA and where less than 5%, and preferably less than 3%, is in the form of DHA is provided for the treatment of a psychiatric or central nervous disorder. The preparation may be administered with conventional drugs to treat psychiatric or central nervous disorders to improve their efficacy or reduce their side effects.

21 Claims, 3 Drawing Sheets

Figure 1. The synthesis of eicosapentaenoic acid from alpha-linolenic acid

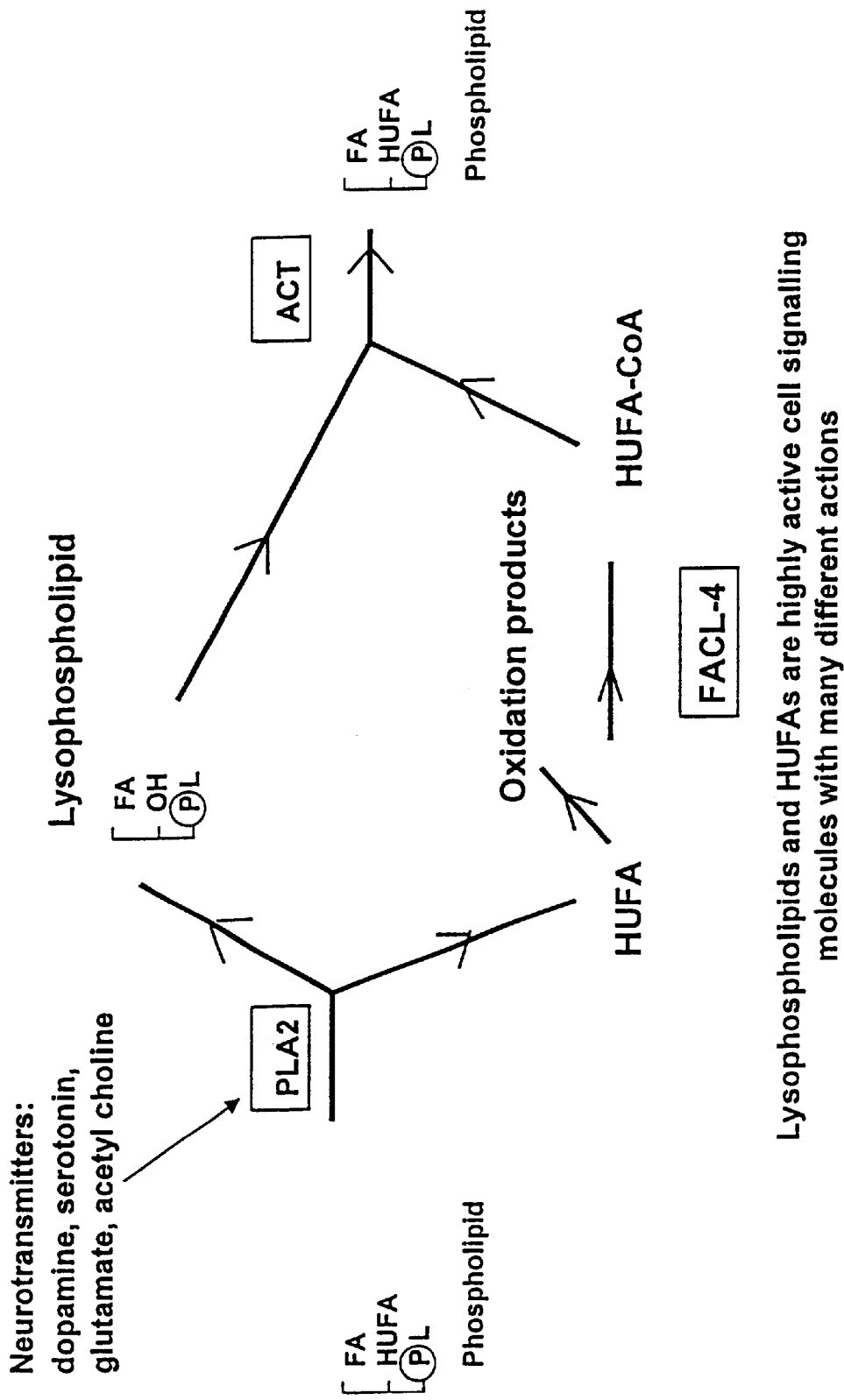

HIGHLY PURIFIED EPA FOR TREATMENT OF SCHIZOPHRENIA AND RELATED DISORDERS

BACKGROUND OF THE INVENTION

Even though many new drugs have been discovered over the past twenty years, psychiatric disorders are still relatively poorly treated. With most psychiatric illnesses, drug treatments do not treat all patients successfully. This is true of schizophrenia, schizoaffective and schizotypal disorders, bipolar disorder (manic-depression), unipolar depression, dementias, panic attacks, anxiety, sleep disorders, attention, hyperactivity and conduct disorders, autism, personality disorders, and all other psychiatric conditions. For example, in depression, standard drugs achieve a 50% reduction in standard depression scores in about two thirds of patients: the others do not respond. In schizophrenia, the average improvements are only of the order of 20–30% (S Leucht et al, Schizophrenia Research 1999;35:51–68) although individual patients may do much better than this.

The same is true of neurological disorders like Alzheimer's disease and other dementias, Parkinson's disease, multiple sclerosis, stroke, epilepsy and Huntington's disease. Again, many patients fail to respond to existing treatments, or respond only to a limited degree. In none of these conditions do existing drugs reliably produce a complete remission of symptoms. There is therefore a great need for new treatments, particularly ones which have novel mechanisms of action.

In PCT filing WO98/16216 attention was drawn to the value of a particular fatty acid, eicosapentaenoic acid (EPA), and its derivatives, in the treatment of schizophrenia, depression and dementias. EPA is a highly unsaturated fatty acid which can be derived from the dietary essential fatty acid, α-linolenic acid by a series of three reactions (FIG. 1). EPA is a fatty acid containing 20 carbon atoms and 5 double bonds, all in the cis-configuration. The double bonds are located at the 5, 8, 11, 14 and 17 positions and the full chemical name is therefore all cis (or all z) 5, 8, 11, 14, 17-eicosapentaenoic acid (or sometimes icosapentaenoic acid). The abbreviation which is always used is EPA. EPA is one of the highly unsaturated fatty acids, the main types of which are shown in FIG. 2. The reactions which convert alpha-linolenic acid to EPA are slow in humans and only a very small proportion of dietary α-linolenic acid is converted to EPA. EPA is also found in marine micro-organisms and, via the food chain, makes up between 3% and 30% of natural marine oils derived from oily fish and marine mammals. EPA is found linked to many different chemical structures. It can be found in the form of phospholipids, tri, di- and monoglycerides, amides, esters of many different types, salts and other compounds. In each case the EPA moiety can normally be split from the complex molecule to give the free acid form which can then be linked again to other complex molecules.

As described in PCT filing WO 98/16216 it was unexpectedly found that an oil enriched in EPA was of value in treating schizophrenia, while an oil enriched in the closely related fatty acid, docosahexaenoic acid (DHA), was not. This was surprising because DHA is found in large amounts in human brain whereas EPA is found only in trace quantities. It was therefore anticipated that DHA would be effective but EPA would not. In fact the opposite was found. WO 98/16216 disclosed the use of EPA and its derivatives for the treatment of psychiatric disorders.

SUMMARY OF THE INVENTION

The present invention provides a pharmaceutical preparation comprising EPA in an appropriately assimilable form where of all the fatty acids present in the preparation at least 90%, and preferably at least 95%, is in the form of EPA and where less than 5%, and preferably less than 3%, is in the form of docosahexaenoic acid. Such preparations are for the treatment of any disorder except peripheral vascular disease and hyper-triglyceridaemia.

Preferably, among the other fatty acids present there are less than 5%, and preferably less than 3%, of each of AA or DPA-n-3, individually. The same preferably applies for any other fatty acids which might compete with the EPA.

It is preferred that the aggregate DHA, AA and/or DPA-n-3 content is less than 10%, of the total fatty acids present, and preferably less than 5%.

The EPA may be in the form of ethyl-EPA, lithium EPA, mono-, di- or triglyceride EPA or any other ester or salt of EPA, or the free acid form of EPA. The EPA may also be in the form of a 2-substituted derivative or other derivative which slows down its rate of oxidation but does not otherwise change its biological action on psychiatric or brain disorders to any substantial degree (N. Willumsen et al., Biochimica Biophysica Acta, 1998, 1369: 193–203).

Such pharmaceutical preparations may be used for the treatment of a psychiatric or central nervous system disorder, including: schizophrenia, schizoaffective disorder or a schizotypal disorder; depression or manic-depression (bipolar disorder); anxiety or panic disorder or social phobia, or a sleep disorder or an attention deficit, conduct, hyperactivity or personality disorder; autism; Alzheimer's disease, vascular dementia or another dementia, including multi-infarct dementia, Lewy body disease and diseases attributable to prion disorders; Parkinson's disease, or other motor system disorder; multiple sclerosis; stroke; epilepsy; and Huntington's disease or any other neuro-degenerative disorder.

The present invention further provides formulations for use in psychiatric and neurological disorders in which a drug which acts primarily on neurotransmitter metabolism or receptors is prepared for co-administration with a pharmaceutical preparation according to the first aspect of the invention, as well as pharmaceutical formulations comprising a preparation according to the first aspect of the invention together with a drug which acts primarily on neurotransmitter metabolism or receptors. The conventional drug may administered in conventional dosage, and the EPA formulations according to the first aspect of the invention administered to the patient separately. The conventional drug may be combined with the EPA preparations of the first aspect of the invention in a combination formulation, or the two may be provided in separate individual formulations but in a combination pack.

The EPA-containing preparations of the present invention may be administered with any drug known to have an effect on the treatment of psychiatric or central nervous system disorders to improve the efficacy of the drug or reduce its side effects.

Suitable drugs for co-administration with the EPA preparations of the first aspect of the invention are clozapine; and any one of the class of typical or atypical neuroleptics, including chlorpromazine, haloperidol, risperidone, olanzapine, sertindole, ziprasidone, zotepine or amisulpiride. Others are mentioned below.

The present invention still further provides a method of treating or preventing the side effects of a drug used in treating psychiatric or neurological disorders by administration of the drug and a pharmaceutical preparation according to the first aspect of the present invention.

BRIEF DESCRIPTION OF THE DRAWINGS

This invention is further understood by reference to the drawings wherein:

FIG. 3 is a schematic showing phospholipid signal transduction.

DETAILED DESCRIPTION OF THE INVENTION

Figure 1:
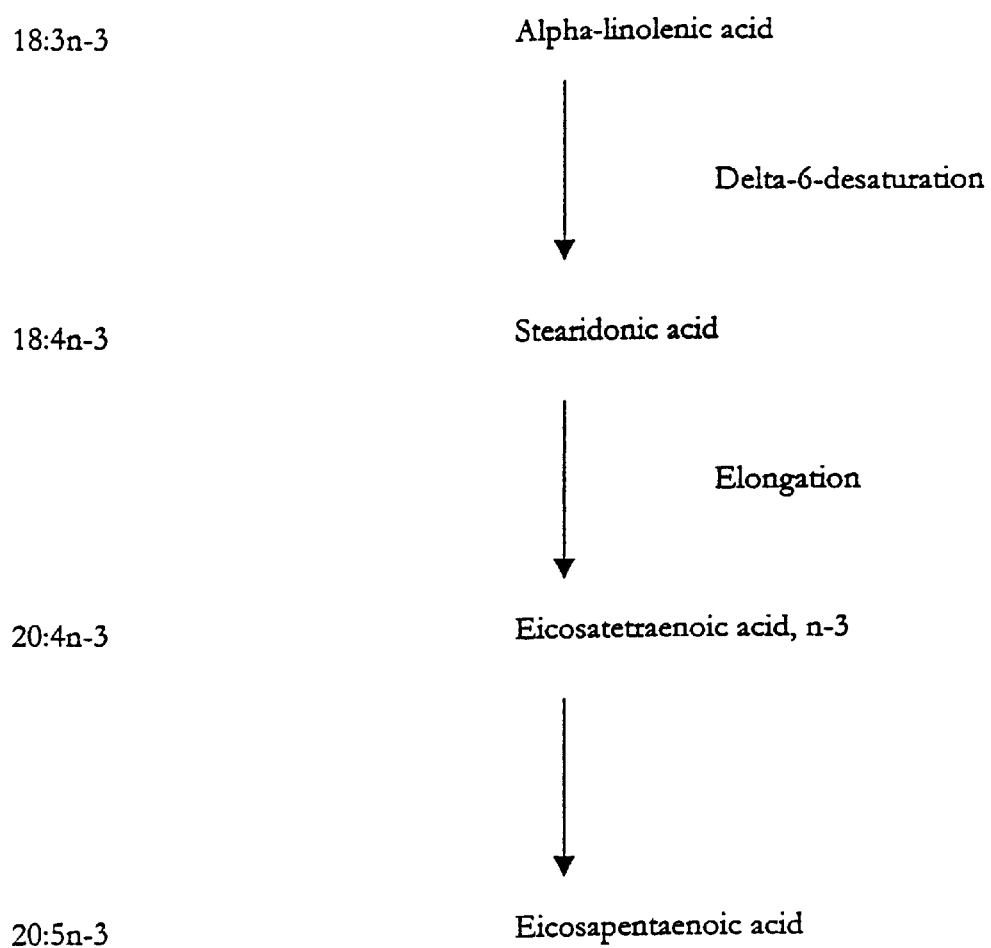
FIG. 1 is a schematic showing the synthesis of eicosapentaenoic acid from alpha-linolenic acid.

It is important in treatment of psychiatric disorders to use pure or nearly pure EPA and EPA derivatives. It is a surprising conclusion that DHA and related fatty acids may not only be ineffective but may actually reduce the efficacy of EPA and its derivatives.

Phospholipids are the main components of nerve cell membranes. In nerve cells the middle carbon atom of phospholipids, known as Sn2, is usually attached to a highly unsaturated fatty acid (HUFA) such as DHA, arachidonic acid (AA), and sometimes EPA. HUFAs are fatty acids containing 18–26 carbon atoms and three or more double bonds. When nerve cells are activated, for example by dopamine or serotonin, the activity of a group of enzymes collectively known as phospholipase $A_2$ ($PLA_2$) is frequently increased. $PLA_2$ releases the HUFA from the Sn2 position, giving a free molecule of HUFA and a molecule of what is known as a lysophospholipid (LyPL) (a phospholipid without a fatty acid attached to the Sn2 position) (FIG. 3). Both of these molecules can be highly active cell signalling agents themselves, and can change cell function in a number of different ways. In addition, the HUFA can be converted to prostaglandins, leukotrienes, hydroxy acids and a whole range of short-lived molecules which regulate neuronal function. For example, one of these molecules derived from arachidonic acid, leukotriene C4, seems to be absolutely required for normal nerve cell growth and development (E Mayatepek and B Flock, Leukotriene C4-synthesis deficiency: a new inborn error of metabolism linked to a fatal developmental syndrome Lancet 1998; 352: 1514–7).

If cell function is to be normal, it is important that this activation should be temporary and should be terminated by removing the free HUFA and the LyPL. Otherwise membrane damage may result because the LyPL can be destructive. Furthermore the free HUFAs are easily oxidised to highly active free radicals which can do great damage. There is an emerging consensus that such membrane damage is a fundamental pathological basis for many neurodegenerative disorders, including Alzheimer's disease and other dementias, Parkinson's disease, stroke, Huntington's disease, all types of ischaemic damage, and multiple sclerosis. A range of initiating causative factors may all cause damage by the same common route. Phospholipid breakdown to LyPLs and free HUFAs may also be important in epilepsy.

The signal transduction processes involving HUFAs and LyPLs are terminated in most cases by a two sequence reaction. First, the HUFA is linked to coenzyme A by a group of enzymes known as fatty acid coenzyme A ligases (FACLs). These enzymes are also known as acyl-CoA synthetases. The HUFA-coenzyme A derivative is then linked to the LyPL by a group of enzymes known as acyl CoA: lysophospholipid acyltransferases (ACLATs) which liberate coenzyme A in the process (A Yamashita et al, Acyltransferases and transacylases involved in fatty acid remodelling of phospholipids and metabolism of bioactive lipids in mammalian cells. J Biochem 122: 1–16, 1997). This sequence thus removes from the nerve cell the HUFAs and the LyPLs and brings to an end the events associated with signal transduction, so preparing the neuron for the next stimulus (FIG. 3).

There is now a substantial amount of evidence which demonstrates that in the three major psychotic mental illnesses there is increased activity of one or more of the phospholipase group of enzymes and particularly in one or more of the $PLA_2$ group. These three illnesses are schizophrenia, bipolar disorder and major depression: the three disorders are often found together in the same families, and often have overlapping ranges of symptoms. It has long been thought that at least part of their biochemical basis is common to all three disorders and it is possible that the $PLA_2$ abnormality constitutes that common factor. In schizophrenia, there are increasing circulating levels of $PLA_2$ in the blood. In bipolar disorder, lithium, which is the main established treatment, has been shown to inhibit the activity of $PLA_2$. In major depression, there is depletion of HUFAs of the n-3 series from membranes, coupled with activation of inflammatory responses which occurs with enhanced activity of $PLA_2$. Each of those illnesses, however, involves more than one biochemical abnormality: while a $PLA_2$ or related phospholipase abnormality may be common to all three, the other abnormalities are probably specific to each disease.

In schizophrenia, it has recently been discovered that there is a second abnormality in the fatty acid cycle. This is a deficit in function of FACL-4, the enzyme which links HUFAs to coenzyme A in human brain (Y Cao et al, Cloning, expression and chromosomal localization of human long-chain fatty acid-CoA ligase 4 (FACL4) Genomics 1998; 49: 327–330). It is known that there is a defect in the incorporation of HUFAs into phospholipids in schizophrenia but the precise enzyme has not been known. However, FACL-4 is found in brain, is specific for HUFAs, and when absent produces both brain abnormalities and also minor physical abnormalities such as a high arched palate which are typical of patients with schizophrenia (M Piccini et al, FACL-4, a new gene encoding long-chain acyl-CoA synthetase 4, is deleted in a family with Alport Syndrome, elliptocytosis and mental retardation. Genomics 1998;47:350–358). It is the combined presence of both the enzyme abnormalities which produces the disease.

The second or other abnormalities in bipolar disorder and in major depression are not yet known. Another phospholipase, PLC, which acts at the Sn3 position to liberate inositol phosphates and diacylglycerol may be involved in bipolar disorder. Both of these molecules, like LyPL and HUFAs, are involved in cell signalling: overactivation of both PLC and $PLA_2$ is likely to be related to bipolar disorder.

In the neurodegenerative conditions there appears to be an uncontrolled activation of membrane degrading enzymes like phospholipases, coupled with increased formation of free radicals associated with the oxidation of HUFAs and the membrane damage produced by LyPL. This type of phenomenon, with membrane damage associated with excess phospholipase activity, has been well described by many investigators in Alzheimer's disease and other dementias, in multiple sclerosis, in stroke and other brain disorders caused by ischaemia or injury, in Parkinson's disease, in epilepsy and in Huntington's disease. In attention deficit disorder, also known as hyperactivity, there are deficits in the blood of the highly unsaturated fatty acids which can be acted upon by phospholipases.

In all of these situations, therefore, there is some evidence of increased phospholipase activity and signal transduction activity which may not be terminated in a normal way. Thus the phospholipases, FACLs and acyl-transferases present new targets for drug action. Our observation that EPA-enriched materials are beneficial in psychiatric disorders may therefore be explained in several ways:

EPA is known to inhibit phospholipase $A_2$ (M J Finnen & C R Lovell, Biochem Soc Transactions, 1991;19:915) and so will help to down regulate the initial activation process. Interestingly, in this assay system, the related fatty acid docosahexaenoic acid (DHA) had no effect.

EPA has an unusually high affinity for the human brain enzyme FACL-4 (Y Cao et al, 1998 see above). Usually with enzymes which act on HUFAs, the activities with HUFAs like EPA, DHA and AA are similar, or very frequently, DHA and AA are more active than EPA. With FACL-4, however, activity for AA was more than twice as great as for DHA, whereas that for EPA was 50% greater than for AA (Y Cao et al, 1998). This means that EPA will more readily than other HUFAs enter the cycle, form an EPA-CoA derivative, link to LyPL and so terminate the activity of free LyPL. Thus EPA will, more effectively than other HUFAs, stop the activation once it has started.

Because EPA will compete with AA for incorporation into the Sn2 position of phospholipids, EPA will also reduce the amount of AA incorporated into that position. This is likely to be particularly important in depression, where AA levels are relatively or absolutely abnormally high.

EPA itself is a HUFA which can be converted to desirable compounds like prostaglandin $I_3$ ($PGI_3$) and prostaglandin $E_3$ ($PGE_3$) which have a range of anti-inflammatory and antithrombotic actions which may be particularly useful in neurodegenerative disorders and in depression. The compounds derived from EPA appear to be less potentially harmful than the equivalent compounds derived from AA. Replacement of AA by EPA is therefore likely to be of particular value in all the neurodegenerative disorders described above, where at least part of the damage is attributable to overactive phospholipases which release AA which can then be converted to pro-inflammatory compounds.

The purification of EPA is difficult and complex. Because its five double bonds must all be in the right positions in the carbon chain and must all be in the cis configuration, EPA is difficult to synthesize. In nature EPA is almost always found mixed with other fatty acids in the forms of triglycerides and phospholipids. The principles of purification of EPA are well known to those skilled in the art and include low temperature crystallisation, urea fractionation, lithium crystallisation, fractional distillation, high pressure liquid chromatography, supercritical carbon dioxide chromatography and various other forms of chromatography using silica gels and other column packings. The application of these known techniques has been difficult to apply in practice on a large scale and only recently has pure EPA (more than 90% pure and preferably more than 95% pure) become available for testing in psychiatric and CNS disorders. In one version of the purification process, natural fish oil triglycerides rich in EPA are saponified and the fatty acids converted to the ethyl ester form. A preparation enriched in ethyl EPA is then prepared by molecular distillation with collection of the appropriate fraction. This fraction is then converted to a preparation containing over 80% of ethyl EPA by urea precipitation. The final preparation of more than 96% pure ethyl EPA is then achieved by either silica gel chromatography or high pressure liquid chromatography.

Conventionally, most studies on the uses of EPA and related fatty acids have used materials partially enriched in EPA but also containing substantial amounts of other fatty acids, especially docosahexaenoic acid (DHA) which is found alongside EPA in most natural oils. The fatty acids have usually been in the triglyceride or ethyl ester forms, and occasionally in the free acid and phospholipid forms. Docosapentaenoic acid (DPA n-3) is also a common component of such materials. The new understanding of possible mechanisms of action of EPA which we have developed has, however, led to the realisation that the purer is the EPA the better is likely to be the activity. This is not just a question of dose, although that is indeed a valuable aspect of the application of pure EPA. From the point of view of a patient, particularly a mentally disturbed patient, it is obviously better to give, say, 1 g of EPA as a 95% pure preparation than, say, 5 g of a 19% pure preparation providing the same total amount of EPA. The patient is much more likely to comply with the lower volumes required with the highly purified compound.

More importantly, other fatty acids such as AA, DPAn-3, and DHA, which are relatively similar in structure to EPA, but do not share the same spectrum of biological activity, compete with EPA for binding to the active sites of all the relevant enzymes. Thus these other fatty acids will compete with EPA for occupation of these active sites and reduce its activity. The purer the preparation of EPA the more likely is it to occupy the relevant active binding sites, and the more likely is it to be able to have desirable biological effects.

Our attention was unexpectedly drawn to the importance of highly purified EPA by our experience with a patient, a depressed women aged 35 years. She had had a long history of depression with Hamilton Depression Rating Scale scores ranging from 15 to 25. Trials of several different antidepressants, including traditional tricyclic compounds and newer selective serotonin reuptake inhibitors had failed to have an impact. Because of evidence of the importance of EPA in depression she was given a three months trial of 4 g/day of an EPA enriched fish oil containing 25% of EPA, together with 8% of DHA and 10% of other highly unsaturated fatty acids. At the start of this trial she had a Hamilton score in the 20–22 range and at the end a Hamilton score in the 16–18 range, a small but not very important improvement. She continued the EPA-rich oil for a further two months without any further change. A 96% pure preparation of ethyl-EPA with less than 3% DHA then became available to me and it was suggested that the woman should switch from taking 4 g/day of the 25% EPA preparation to 1 g/day of the 96% preparation. We expected is that this would be more convenient but did not expect any clinical improvement because the EPA daily dose remained unchanged. However, surprisingly, after about 3–4 weeks she began to experience a major improvement with Hamilton scores falling below 6 for the first time for several years. As a result of this, and of thinking about the evidence relating to the binding of EPA to FACL-4 and presumably to other proteins, we came to the conclusion that it was important for clinical efficacy to administer EPA in a highly purified form for maximum clinical effectiveness. Surprisingly, the same daily dose of EPA in a purified form seems considerably more effective than that dose when mixed with other fatty acids which may compete with EPA for binding to the relevant sites of action.

This initial experience has now been confirmed by many other case reports in a range of psychiatric disorders. Some examples of the observations made include the following:

Schizophrenia: A patient with a ten-year history had been well controlled by taking 16×0.5 g capsules a day of fish oil containing 24% of EPA and 8% of DHA. This provided around 1.9 g/day of EPA and 0.6 g/day of DHA. He was not taking other antipsychotic drugs. However, he did not like taking the high doses of fish oils and tried to reduce the dose. However, when he did this the symptoms returned and it was concluded that he had to take around 2 g/day of EPA to remain well. When the purified ethyl-EPA became available, he was switched to 4×0.5 g capsules, also providing around 2 g/day. This controlled his symptoms very well. He therefore dropped the dose to 1 g/day. Unlike the previous situation with the mixed fish oil providing 1.9 g/day of EPA and 0.6 g/day of DHA, reducing the ethyl-EPA dose to 1g/day did not lead to a recurrence of symptoms. 1 g/day in pure form therefore appeared as effective and possibly more effective than 1.9 g per day of EPA when mixed with DHA and other fatty acids.

Bipolar disorder: Bipolar disorder is a condition in which either a depressive or a manic state is episodic, or in which depressive or manic states alternate. The standard treatments are lithium or valproate derivatives, or the antipsychotic neuroleptic drugs which are particularly used to control the manic states. Standard antidepressants are sometimes used but they have to be applied with caution because there is a risk that they may precipitate a manic state.

Very high doses (9–10 g/day) of mixed EPA and DHA have been reported to be helpful in managing bipolar patients, improving depression and reducing the risk of relapse into either a depressive or a manic episode (A Stoll et al, Omega-3 fatty acids in bipolar disorder. Archives of General Psychiatry, 1999; 56: 407–412). Prior to the availability of the pure ethyl-EPA, five patients with bipolar disorder, whose condition was only partially controlled by lithium with intermittent neuroleptics to control the manic episodes, were given 10–20 g/day of a fish oil containing 18% of EPA and 12% of DHA. This provided 1.8–3.6 g of EPA and 1.2–2.4 g of DHA per day. On this treatment the patients were less depressed, and less prone to mood swings, as indicated by following their clinical course for over a year. They were, however, far from completely normal. When the pure ethyl-EPA became available, they were switched from the fish oil to the pure EPA at a dose of 2 g/day in the form of four 0.5 g soft gelatin capsules. In each case their clinical condition improved considerably. Their depressions became substantially better and they showed less tendency to mood swing. In particular they all noted an improvement in something which is difficult to measure by conventional psychiatric rating scales. This is a sense of inner tension or dysphoria, a state which is associated with the illness, but which may be exaggerated or changed by antipsychotic drugs to a state of confused tension, sometimes described as a sense of the brain being replaced by cotton wool, and a difficulty of thinking clearly in a straight line. Remarkably, the patients reported that this sense of dysphoria, tension and "cotton-wool thinking" was greatly reduced or disappeared altogether. They had not noticed this effect which being treated with the higher dose of EPA in the form of the EPA/DHA mix in fish oil. Thus again the purified EPA had a greater and qualitatively different effect from the mixed EPA and DHA, supporting the idea that DHA actually reduces the therapeutic effect of EPA, and that highly purified EPA is therapeutically more effective.

Attention deficit hyperactivity disorder (ADHD): ADHD and closely related conditions like attention deficit disorder and conduct disorders are commonly found in children. Occasionally they may be successfully treated by behaviour modification and other psychological techniques or by careful attention to diet. However, in most cases, paradoxical treatment with one of the stimulant drugs related in their action to amphetamine is required. Methylphenidate and dextroamphetamine are the commonest used. A seven year old boy with serious ADHD since infancy was driving his parents to distraction. Psychological measures and diet had completely failed, and his condition was only partially controlled by methylphenidate. The parents were concerned about the long term consequences of stimulant drugs. The boy was therefore tried on two capsules of pure ethyl-EPA per day. There was little change for the first two weeks but then a substantial improvement in behaviour developed. The boy became less tense and irritable, less hyperactive, more open to reasoned discussion and enormously less disruptive both at home and school. Even when his methylphenidate was stopped, his behaviour remained improved.

Dementia: A 75 year old woman developed dementia, probably of Alzheimer type but possibly with multi-infarct contributions because of associated cardiovascular disease. As often occurs she also became withdrawn and depressed but, unfortunately, this state was interrupted by irrational and violent outbursts, usually directed at members of her family, but also sometimes against complete strangers. She was tried on two cholinergic drugs: although these produced a small improvement in her cognitive state they did nothing for her depression, irritability and anger. She was tried on a dose of 4× 0.5 g capsules of pure ethyl-EPA, two given in the morning and two in the evening. Within four weeks she had experienced a remarkable improvement, becoming more cheerful and friendly and showed a substantially reduced irritability. Her family also thought her cognition had improved but this is difficult to be certain of because of her improved mood.

Panic and anxiety disorders are very common. They are associated with panic attacks which may come out of the blue with no precipitating factors at all, or may be associated with mildly stressful situations which in normal people would evoke no such reactions. The characteristics of panic attacks are a feeling of severe anxiety, difficulty in breathing, sweating, a feeling of abdominal discomfort known as "butterflies in the stomach" and a feeling of legs collapsing. Very frequently associated with all these psychological symptoms, there is also a tachycardia, which is associated with a subjective sensation of cardiac palpitations. Insomnia is common, and patients frequently wake up spontaneously in the middle of the night with palpitations and panic. Patients are also frequently depressed. Common treatments include anti-anxiety drugs such as benzodiazepines, beta-blockers to control the palpitations and anti-depressants.

We have now treated several patients who have panic and anxiety disorders with purified ethyl-EPA with excellent effect. Three case histories follow. A 29 year old woman was disabled as a result of frequent and uncontrollable panic attacks and palpitations. Treatments with benzodiazepines, beta-blockers and antidepressants had proved only partially effective in controlling her symptoms. She was then given a dose of 2 g per day of ethyl EPA as four 500 mg capsules. Her symptoms dramatically improved and over a period of three months her panic attacks and palpitations were almost absent, with only two relatively mild attacks. This treatment was much more effective than any previous treatment she had received. A 56 year old woman had suffered from mild anxiety and panic attacks for most of her life but these had become much worse over the previous few years in association with various problems with her children. Anxiolytics and antidepressants had only modest effects and her palpitations were uncontrolled even by relatively high doses of beta-blockers. Again she was treated with ethyl-EPA over a period of four months. Her anxiety and panic attacks became much less severe, and even when they occurred were free of palpitations which had previously worried her a great deal. The third patient was a 55 year old housewife who had been through two divorces and was now in a long-term relationship. She had several panic attacks every week, sometimes in the middle of the night, and always accompanied by strong palpitations which were very worrying for her. These panic attacks were accompanied by depression. She was very reluctant to go out for fear of having an attack and this seriously disrupted her life. Again, antidepressants, beta-blockers and anxiolytics had had only limited beneficial effects. She was also treated with ethyl-EPA and over a period of four months experienced a dramatic reduction in her panic attacks and palpitations. Sometimes, she felt that an attack of palpitations might be coming on but it rarely materialised. As a result, she felt increasing confidence and was able to resume a much more normal life. These observations demonstrate that purified ethyl-EPA is effective in the management of panic disorder.

Another use for ethyl-EPA is as an adjunct to the management of severe depression when using electroconvulsive therapy (ECT). ECT is used most other treatments have failed to be helpful. It involves the administration of shocks under anaesthesia and, although effective, is used with reluctance by both patients and doctors because of fears that it may damage the brain and cause memory loss. Anything from five to twenty or even more shocks may be given during a course of treatment. It would be highly desirable to be able to limit the numbers of shocks required to achieve a beneficial effect and in a small number of patients we have found that this is indeed the case.

These observations indicate that pure ethyl-EPA is of value in a wide range of psychiatric and neurological disorders, reflecting the common involvement of membrane and phospholipid abnormalities in these conditions.

But E-EPA is not only useful as a therapy by itself. E-EPA can be co-administered with standard drugs used in various psychiatric and neurological conditions and can substantially enhance the response to standard therapy, and also reduce many of the side effects of standard therapy. The present invention provides combination therapy involving the co-administration of E-EPA with standard drugs, either involving the same formulation or the same packaging.

Our attention was drawn to this possibility by a striking case history. A middle aged male patient with a long history of schizophrenia had failed to respond to therapy with "typical" neuroleptics. "Typical" neuroleptics are drugs with a strong blocking action on dopamine $D_2$ receptors (B Leonard, Fundamentals of Psychopharmacology, $2^{nd}$ edition, Wiley, New York, 1997). This mechanism is thought to be responsible for their rapid effects on the so-called "positive" symptoms of schizophrenia (such as hallucinations, delusions and thought disorder). These drugs, however, have little effects on the so-called "negative" symptoms of schizophrenia such as anhedonia, lack of affect, and emotional and social withdrawal. The $D_2$ blocking action is also responsible for many of the adverse effects of these drugs, which include extrapyramidal movement disorders, excess prolactin secretion, and tardive dyskinesias. Examples of widely used drugs in this class include chlorpromazine, thioridazine, haloperidol, pimozide, flupenthixol and sulpiride.

In spite of treatment with full doses of several of these drugs the patient failed to respond. He was therefore put on the first of the so-called "atypical" neuroleptics, clozapine. These atypical drugs have a much lower affinity for $D_2$ receptors, and often have a wide range of other receptor actions. These may include blockade of one or more of the other dopamine receptors such as $D_1$, $D_3$ or $D_4$, and also usually including blockade of one or more classes of serotonin receptors. They do not cause much prolactin secretion and rarely cause extrapyramidal movement disorders. They may also have actions at other receptors, including histamine, glutamate and acetyl choline receptors. Drugs in this class include clozapine, olanzapine, quetiapine, risperidone, ziprasidone, sertindole and perhaps zotepine and amisulpiride. There are many drugs of this type in early development, all characterised by a lower affinity for $D_2$ receptors than the "typical" neuroleptics.

The patient was treated with clozapine, eventually reaching a maximum dose of 900 mg/day. This produced some improvement but the patient remained severely ill. He was tense, withdrawn and suspicious and exhibited bizarre behaviour. For example, he refused to allow any sound when he turned on the television set because of his paranoia about people speaking to him. This was naturally irritating to anyone attempting to watch television with him. The patient was given trials of olanzapine, quetiapine and risperidone with no substantial benefit. Clinically he appeared to do best on clozapine and so was maintained for many months on 900 mg/day. The main side effect of clozapine which bothered him was the hypersalivation.

E-EPA in a dose of 2 g/day was then administered in addition to clozapine. Although EPA is an effective treatment for schizophrenia, its onset of action is slow and substantial benefits are not normally seen until 4–8 weeks after starting treatment (B Puri et al, Sustained remission of positive and negative symptoms of schizophrenia following treatment with eicosapentaenoic acid, Archives of General Psychiatry 55:188–189, 1998). However, in this clozapine-treated patient who had been so seriously ill for many years, the effects began to be apparent within days and were dramatic within two weeks. They were noted both by the patient himself and by family and friends. In particular, instead of being depressed he became cheerful, instead of being tense he became relaxed, instead of being withdrawn and refusing to speak, he become outgoing and chatty. For his family and friends, one of the first and most striking effects was that he allowed the television to be on with a normal sound level. The psychiatrist in charge of the patient noted "I cannot remember ever seeing such a dramatic improvement in a schizophrenic illness in less than 2 weeks". A particularly important aspect of this case is that the clozapine-induced hypersalivation was considerably reduced.

In this patient, clozapine and other neuroleptics, both typical and atypical, clearly had very limited beneficial effects. On the other hand E-EPA had a surprisingly large and unexpectedly rapid effect which is not normally seen if E-EPA is administered alone. This suggests a strong beneficial interaction between clozapine and E-EPA and suggests that clozapine and E-EPA should be administered together in at least some patients.

There are good reasons why E-EPA should have additive and even synergistic effects in association with conventional psychotropic drugs, not only for schizophrenia but also for all other psychiatric and neurological disorders. This is because most drugs used for the management of psychiatric and neurological disorders act on neurotransmitter metabolism or on neurotransmitter receptors, modulating the synthesis, inactivation, reuptake or responses to neurotransmitters such as noradrenaline, serotonin, dopamine, glutamate, acetyl choline, and gamma-aminobutyric acid (GABA). However, many phenomena in nerve cells occur after a receptor has been occupied by a neurotransmitter or blocking agent. Receptor occupation leads to many changes in cellular function which go under the general name of "signal transduction" or "cell signalling" and which include changes in G proteins, in calcium movements, in sodium and potassium movements, in metabolism of phospholipids and eicosanoids, in cyclic nucleotide changes, and in gene regulation. These are only some examples of the processes which take place under the general heading of signal transduction. The specific example of activation of the $PLA_2$ cycle which may follow activation of dopamine, serotonin, acetyl choline or glutamate receptors is shown in FIG. 3.

There is increasing evidence that some of the abnormalities which cause psychiatric and neurological disorders are not at the neurotransmitter or receptor level but are at the post-receptor signal transduction level. Much of this evidence in relation to psychiatric disorders has been summarised in a recently published book (Phospholipid Spectrum Disorder in Psychiatry, ed. M Peet, I Glen & DF Horrobin, Marius Press, Carnforth, UK, 1999). If this is so, then drugs like most of these currently in use, which act at the neurotransmitter or receptor level, will only have limited efficacy. This is true of drugs for many types of psychiatric and neurological disorders, most of which have their primary actions at the neurotransmitter or receptor level. Diseases currently treated by drugs affecting neurotransmitter metabolism or neurotransmitter receptors include schizophrenia, depression, bipolar disorder, attention deficit, conduct and related disorders, Parkinson's disease, dementias, anxiety, panic and social phobic disorders, and premenstrual syndrome. The current drugs would be expected to have additive or synergistic effects with drugs which act at the post-receptor signal transduction level, since then the drug combination would be acting at two different levels in the neuron.

The main effect of E-EPA is to modulate post-receptor phospholipid-related signal transduction. Indirectly these actions then modulate other processes or enzymes such as protein kinases, calcium movements, cyclic nucleotide metabolism or gene expression. There are therefore strong and potentially valuable interactions between EPA and any of these other classes of drug.

This case history of the single patient has unexpectedly drawn our attention to a general principle, namely the idea that E-EPA or indeed any other form of biologically active EPA may be usefully co-administered with any psychotropic or neurological drug which primarily acts on neurotransmitter metabolism or neurotransmitter receptors.

The drugs which may usefully be co-administered with EPA include typical and atypical antischizophrenic drugs, antidepressants of all classes, drugs used in control of anxiety or panic, drugs used to regulate sleep, and drugs used in the management of Parkinson's disease or dementia. All these drugs act primarily at the level of neurotransmitters or their receptors.

The general principle that E-EPA can potentiate the effects of standard drug treatments can be illustrated by further case histories. A 50 year old man who suffered from severe depression had been tried on several antidepressants without effect. Eventually he was treated with a selective serotonin reuptake inhibitor (SSRI) called citalopram which, surprisingly, relieved some of his depression even though other SSRIs had failed. This produced an improvement which was sustained for several months although during this time he continued to be moderately depressed. In addition to citalopram he was then given 1 g/day of ethyl-EPA. After four weeks, for the first time in several years, he experienced a lightening of mood and regained much of the interest in life which he thought he had lost forever. Another case was a young woman of 21 who dropped out of college with a schizophrenic breakdown. She experienced auditory hallucinations which kept telling her that one of her professors was out to destroy her college career, she became totally distrustful about her close student friends, and she produced a bizarre series of assignment essays which illustrated severe thought disorder. She was treated with 10 mg/day olanzapine which stopped the hallucinations, reduced the paranoia and thought disorder but, she claimed, made her dysphoric and "fuzzy" and unable to think clearly. It also made her very sleepy, and gave her a large appetite causing her to put on weight. She was given 2 g/day ethyl-EPA and after about 4 weeks claimed to be thinking more clearly, and to have a reduced appetite allowing her to lose weight. After a year she was able to return to college where again she consistently performed at the A and B grade level.

A 40 year old man had become ill with schizophrenia at the age of 25. He had florid hallucinations and paranoia, but also withdrew himself from most of his friendships and lived alone. He was tried on various drugs, some of which produced side effects which he did not like. Eventually a dose of the typical neuroleptic, haloperidol, was found which stopped most of the hallucinations and kept his paranoia within reasonable bounds, but seemed to make him even more withdrawn. He lived alone, ceased to communicate with most of his friends, and went around to town alone and muttering to himself. His psychiatrist heard about ethyl-EPA and decided to try it in addition to the standard drug. After eight weeks on treatment with 4 g/day his outlook was transformed. His residual hallucinations disappeared and he became emotionally much warmer and more friendly. He was even persuaded to go on holiday with his family where he enjoyed himself and made new friends. The EPA therefore reversed the extreme withdrawal which appeared to have been exaggerated by haloperidol.

The typical neuroleptics in some patients produce a distressing condition called tardive dyskinesia. This is due in part to irreversible changes in the brain since the condition often does not remit if drug treatment is stopped. The patient experiences uncontrollable twitching and other movements. These can affect any part of the body but commonly affect the face where they are particularly distressing. Facial twitches and movements, including protrusions and uncontrollable movements of the tongue occur. Several patients we have treated with EPA have experienced substantial relief from tardive dyskinesia. Movements have become substantially less and in some patients have disappeared completely.

Clozapine is regarded as a particularly effective drug by many psychiatrists but it has a range of severe side effects. From the patient's point of view one of the most troublesome is hypersalivation. This may not sound very serious but the constant flow of large volumes of saliva is in fact very distressing for the patient and for those who are associated with the patient. The mechanism of the hypersalivation is unknown. Completely unexpectedly, in three clozapine-treated patients for whom hypersalivation was a major problem, treatment with ethyl-EPA not only caused a substantial improvement in psychiatric state, but also dramatically reduced the salivation to normal levels to the great relief of the patients and their carers.

Obesity is another common side effect of antipsychotropic drugs. In this respect some of the newer drugs like olanzapine frequently seem to be even worse offenders than the typical neuroleptics. A young woman who had had a schizophrenic breakdown in her early-twenties had been treated with typical neuroleptics for about 10 years and then for the past two years with olanzapine. She preferred the olanzapine but it still left her withdrawn and unable to communicate normally with friends or family. To her distress it caused her to put on over 10 kg in weight. Her doctor decided to test ethyl-EPA in addition to olanzapine. Over the next six months her withdrawn state gradually improved and she began to perform again as a musician which she had not done for several years. Equally important for her self-esteem she lost most of the weight which she had gained when she first started on olanzapine.

These case histories clearly demonstrate the following:
1. Pure ethyl-EPA has strong therapeutic effects in its own right on schizophrenia, bipolar disorder, depression, attention deficit disorder and dementia. Like other drugs with antipsychotic actions it is likely to have some beneficial effects in most psychiatric disorders and also in neurological disorders associated with membrane damage. These include the various types of dementia (including Alzheimer's disease, multi-infarct vascular dementia and Lewy body disease), multiple sclerosis, Parkinson's disease and Huntington's chorea.
2. Pure ethyl-EPA enhances the beneficial effects of a wide range of psychiatric and neurological drugs. This makes a great deal of sense since it is increasingly apparent that many abnormalities in psychiatry and neurology lie beyond the neurotransmitter receptor in the signal transduction systems of neurons and other cells. EPA acts on these signal transduction systems, providing a rational explanation for the positive interactions between EPA and other drugs.
3. Completely unexpected was the ability of EPA to reduce the adverse effects of psychiatric and neurological drugs. The mechanism is unknown but it appears to be a relatively general phenomenon as it has been noted with drug-induced obesity, movement disorders, sedation, dysphoria and salivation.

Although the case reports of the effects of ethyl-EPA are convincing and in some cases dramatic, unequivocal proof of its efficacy must come from randomised, placebo-controlled trials. We therefore set up a randomised, placebo-controlled study of EPA in 34 patients who had schizophrenia according to the criteria set out in the American Psychiatric Association's Diagnostic and Statistical Manual of Mental Disorders (4$^{th}$ edition, DSM-IV). All of these patients were being treated with clozapine drugs but all remained seriously ill, with schizophrenic symptoms. Like many schizophrenics, some of the patients were also depressed. All were assessed at baseline and after 12 weeks using the Positive and Negative Symptom Scale for Schizophrenia (PANSS) and the Montgomery-Asberg Depression Rating Scale (MADRS).

After giving informed consent, all the patients were randomised on a double blind basis to one of three groups: placebo, or 1 g or 2 g of ethyl-EPA per day in the form of 0.5 g capsules. Placebo and EPA capsules were indistinguishable from one another in appearance.

The percentage changes from baseline in the four groups are shown in the table. All the patients improved to some degree so all the changes are percentage improvements

| rating scale | Placebo | 1g EPA | 2g EPA |
| --- | --- | --- | --- |
| Total PANSS | 5.2% | 18.8% | 17.1% |
| positive PANSS | 9.5% | 20.0% | 25.0% |
| negative PANSS | 11.1% | 22.7% | 22.7% |
| MADRS | 13.3% | 35.7% | 35.7% |

As can be seen, on all the rating scales the EPA groups did substantially better than the placebo group. E-EPA (ethyl-EPA) was effective in reducing symptoms of schizophrenia, symptoms of depression and side effects of existing drugs. The simultaneous effect on depression, as indicated by the MADRS scale, and schizophrenia, as indicated by the PANSS scale, is particularly important. These results therefore confirm the individual patient reports and demonstrate unequivocally that E-EPA has a strong therapeutic effect.

Of particular note is the fact that there were no reported side effects attributable to the E-EPA and no differences at all between placebo and active treatment in the side effects which were reported. This means effectively that, in dramatic contrast to almost all other drugs used in psychiatry or neurology, EPA has no important side effects at all.

Huntington's disease is in many respects the most devastating of all diseases which affect the brain. It is a dominantly inherited genetic disorder which usually becomes manifest between the ages of 30 to 50 and leads to death after a course which usually lasts about 15–25 years. Half of the children of patients will also develop the disease (W J Koroshetz, pp. 654–661 in "Office Practice of Neurology, ed M A Samuels & S Feske, Churchill Livingstone, New York, 1996).

The affected gene is for a protein called huntingtin located on chromosome 4p16.3. The gene contains a polymorphic trinucleotide CAG repeating area. In normal individuals the number of CAG repeats is usually less than 35, whereas in Huntington's disease the number of repeats is higher than this. The longer the number of repeats, the earlier the disease is likely to develop. The repeats result in overexpression of huntingtin which forms aggregates in the affected neurons. The aggregates may be associated with membranes and with the cytoskeleton and cause malfunction and eventually death of the neurons concerned. There can be damage to almost any part of the brain but it is particularly evidence in the basal ganglia structures, the caudate and the putamen.

Several other neurological diseases are now known to be associated with excessive numbers of trinucleotide repeats in other genes. It is believed that similar mechanisms of protein accumulation and neuronal damage may be involved (ST Warren, The expanding world of trinucleotide repeats, Science 1996; 271:1374–1375: P Djion et al, Coden repeats in genes associated with human diseases, Proceedings of the National Academy of Sciences of the USA 1996; 93:417–421). In addition to Huntington's disease, the illnesses known to be caused in this way include fragile X syndrome, Friedreich's ataxia, spinal and bulbar muscular atrophy, spinocerebellar ataxia type I, dentato-rubral-pallidoluysian atrophy, Haw River syndrome, Machado-Joseph disease, and myotonic dystrophy.

Huntington's disease can manifest an extraordinary wide range of symptoms and signs (W J Koroshetz, 1996) and can exhibit features of schizophrenia, depression, anxiety, irritability, loss of emotional control, epilepsy, Parkinson's disease and dementia. It has been suggested that the fundamental end mechanism in a wide range of neurological diseases, including Huntington's disease, amyotrophic lateral sclerosis, Parkinson's disease, Alzheimer's disease and other dementias, and cerebellar degeneration is oxidative damage to membranes and to proteins (M F Beal, Aging, energy and oxidative stress in neurodegenerative diseases, Annals of Neurology 1995; 38: 357–366). It is postulated that in these diseases, normal or abnormal proteins aggregate and damage internal and external membranes. The differences between the diseases relate to the nature of the proteins and to the site of the neurons most affected, but the overall processes are similar.

In a typical patient with Huntington's disease, the illness beings with mild motor incoordination, forgetfulness, slowness to perform actions and emotional liability with irritability. The incoordination then progresses to obvious neurological damage with sudden jerking movements, and repeated uncontrollable writhing and restlessness, a pattern going under the general name of chorea. There is often marked weight loss, possibly in part related to the "exercise" produced by the uncontrollable movements. Eventually the patient ceases to be able to walk, becomes demented with severe memory loss, and requires 24 hour nursing care. Death is often caused by pneumonia due to aspiration of food or liquid into the lungs as a result of inability to swallow normally.

No known treatments are of any substantial value. The abnormal movements and the psychosis may respond partially to standard anti-schizophrenic drugs, while antidepressants, tranquillizers, and anti-epileptic drugs may help to relieve some symptoms transiently. Nothing stops the inexorable downhill course.

Because early Huntington's disease may present with schizophrenia-like features, a randomised trial of 96% pure ethyl-EPA was set up in seven severely disabled patients in the final stages of Huntington's disease. All required 24 hour nursing care, had severe movement disorders, were irritable and were partially demented. They were randomised on a double blind basis to receive 2 g/day ethyl-EPA or 2 g/day placebo for 6 months. During the 6 month period, four patients showed progressive deterioration while three patients reversed the course of the disease and showed improvement with reduced abnormal movements, reduced emotional liability and irritability and improved memory and cognitive function. When the code was broken all four patients who deteriorated were found to be on placebo, while all three patients who improved were found to be taking ethyl-EPA. In four of the patients, two on ethyl-EPA and two on placebo, the brain degeneration was assessed at the beginning and end of the study by magnetic resonance imaging (MRI). MRI allows an accurate assessment of the size of the lateral ventricles, the fluid-filled spaces within the cerebral hemispheres. As Huntington's disease progresses, the lateral ventricles enlarge indicating loss of brain tissue. In the two patients on placebo over 6 months the ventricles enlarged as expected. In the two patients on ethyl-EPA, the MRI showed a reduction in lateral ventricle size indicating an actual reversal of brain tissue loss.

These dramatic results in patients in the end stage of a previously untreatable disease caused by abnormal protein accumulation demonstrate the value of ethyl-EPA in neurodegenerative disorders. Such disorders are all associated with membrane damage, oxidative stress and activation of phospholipases. EPA is able to repair membranes, to inhibit phospholipases and to enhance antioxidant defences. The Huntington's results therefore support the use of pure ethyl-EPA in the neurological disorders associated with trinucleotide repeats, and those associated with oxidative membrane damage which may sometimes be due to abnormal protein accumulation, including Alzheimer's disease and other dementias, Lewy body dementia, Parkinson's disease, epilepsies, multiple sclerosis, stroke and head injury and post-stroke and post-injury syndromes, and diseases of animals and humans due to prion accumulation such as kuru, bovine spongiform encepholopathy, Creutzfeldt-Jacob disease and scrapie.

Very recently it has been shown that Huntington's disease is associated with activation of an enzyme called caspase I or interleukin converting enzyme (ICE). This enzyme is involved in a wide range of neurodegenerative brain diseases. It generates interleukin-l-beta which activates a wide range of pro-inflammatory, cell-damaging actions (VO Ona et al, Inhibition of caspase-I slows disease progression in a mouse model of Huntington's disease. Nature 1999; 399: 263–267). One possible additional mechanism of ethyl-EPA action is therefore inhibition of caspase-I.

The present invention has identified ethyl-EPA as being highly effective. However, it is likely that any form of highly purified EPA which is able to raise EPA levels in the blood is of value in psychiatric disorders. These EPA compounds will all be of value in the treatment of psychiatric and neurological disorders when prepared in pure form. It will always be important to keep to the absolute minimum the presence of related fatty acids, which might interfere with the EPA. The compounds which are known, but which have not previously been prepared or proposed in such pure forms for use in psychiatric and CNS disorders are:

1. Ethyl-EPA which is widely used in Japan for the treatment of cardiovascular disorders.
2. Lithium-EPA which was previously disclosed in U.S. Pat. No. 5,252,333 but which was not then distinguished from any other lithium HUFA derivative as being of particular value in psychiatric disorders. The value of this derivative lies in the fact that lithium itself is a treatment of choice in bipolar disorder and is also known to have therapeutic effects in schizophrenia, schizoaffective disorder and depression. Recently it has been demonstrated that inhibition of PLA2 and of the PLC inositol phosphate cycle are important actions of lithium. Since EPA has related actions, the lithium derivative of EPA will be of particular value.
3. Triglycerides, monoglycerides or diglycerides in which more than 90% and preferably more than 95% of the fatty acids present in the molecule consist of EPA.
4. Other esters and compounds capable of delivering fatty acids to the body in which more than 90% and preferably more than 95% of the fatty acids present are in the form of EPA.

In each of the above cases there should be less than 5% and preferably less than 3% of DHA, DPA or AA or other competing fatty acids individually. In aggregate there should be less than 10% and preferably less than 5% of these competing fatty acids.

These compounds, in 90% and preferably 95% or even purer forms, may all be administered orally via delivery systems known to those skilled in the art, including soft and hard gelatin capsules; microcapsules in powder, tableted or capsule form; tablets for the solid compound, lithium-EPA; or emulsions made with appropriate natural or synthetic emulsifying agents, including phospholipids or galactolipids. The compounds may also be administered parenterally, either directly, or formulated in various oils or in emulsions or dispersions, using either intravenous, intraperitoneal, intramuscular or sub-cutaneous routes. Topical applications using patch technology or vaginal or rectal forms of application are within the range of the invention.

The EPA compounds may advantageously in some patients be coadministered with other drugs used in psychiatry and neurology. Such drugs may include drugs of the typical neuroleptic class such as chlorpromazine, haloperidol, thioxanthene, sulpiride, droperidol, perphenazine, loxapine, thioridazine, fluphenazine, pericyazine, methotrimeprazine or pimozide among others: clozapine: drugs of the atypical neuroleptic class including olanzapine, risperidone, sertindole, ziprasidone, quetiapine, zotepine and amisulpiride; drugs which have antidepressant actions including tricyclic and related antidepressants, noradrenaline reuptake inhibitors, serotonin reuptake inhibitors, monoamine oxidase inhibitors and drugs with atypical antidepressant actions: drugs for sleep disorders, anxiety disorders, panic disorders, social phobias, conduct disorders, personality disorders and attentional deficit hyperactivity disorder; drugs for any form of dementia, including Alzheimer's disease, vascular and multi-infarct dementias, Lewy body disease and other dementias; drugs for any form of neurological disease including Parkinson's disease, multiple sclerosis, Huntington's disease and other neurodegenerative disorders.

In each of the above cases, the EPA compound and the other drug may be administered separately, each in their own formulation. They may be packaged separately or be present in the same overall package. Alternatively, using techniques well known to those skilled in the art, the EPA and other drug may be formulated together, so that a daily dose of EPA of 0.1 g to 10 g per day, and preferably of 0.5 g to 5 g per day, is provided with the normal daily dose of the other drug.

When supplied alone, the useful daily dose of EPA may be in the range of 0.05 g to 50 g/day, preferably 0.1 g to 10 g/day and very preferably 0.5 g to 5 g/day.

It has previously been suggested that omega-3 fatty acids like EPA may be valuable in the treatment of inflammatory disorders of the joints, respiratory system, gastro-intestinal system, kidneys, skins, reproductive system and all other organs. However, the importance of the purity of EPA has not previously been recognised. The invention will therefore be valuable in these disorders also and the present invention also provides pharmaceutical compositions for the treatment of such inflammatory disorders.

Figure 2:
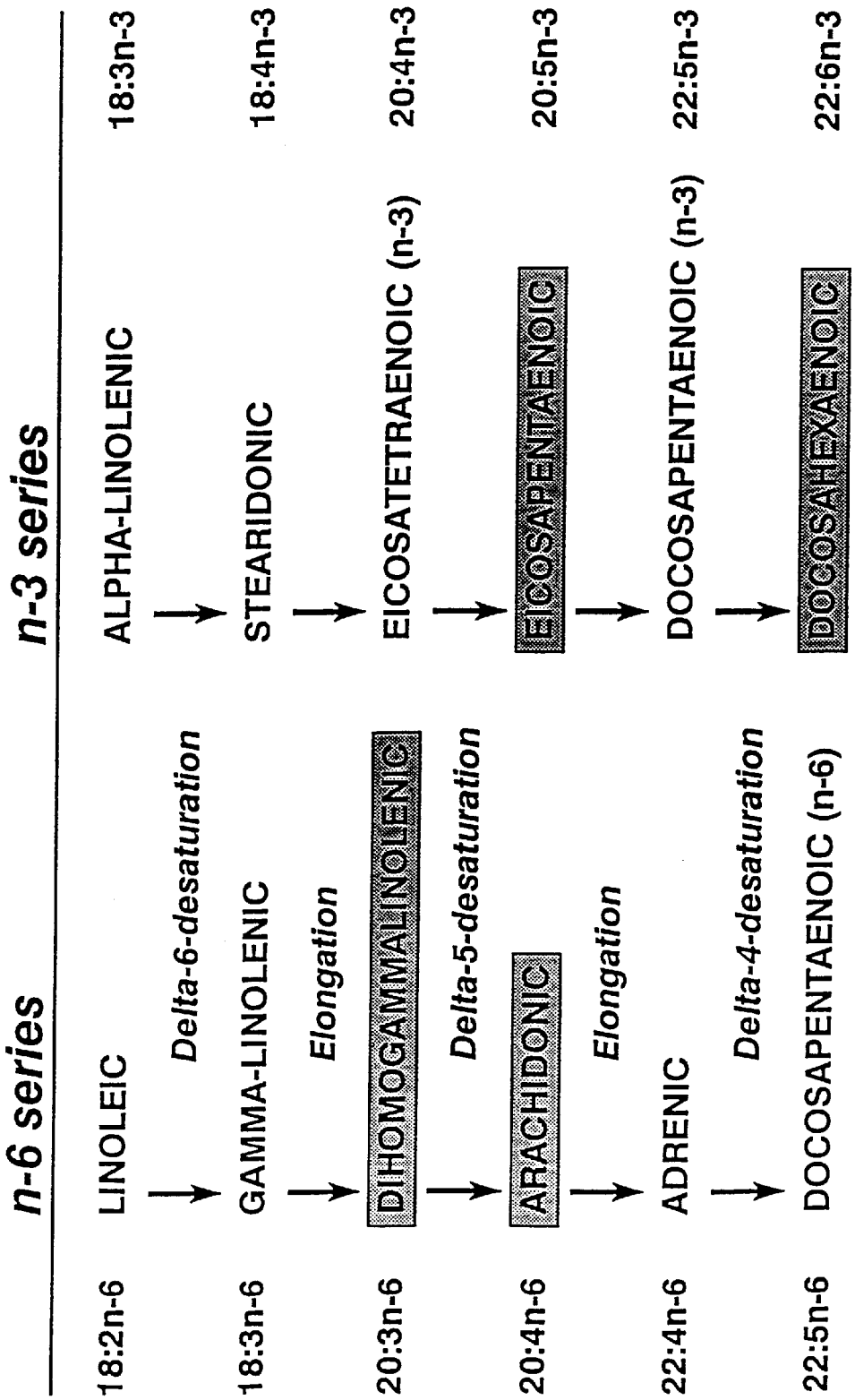
FIG. 2 is a schematic showing the metabolism of essential fatty acids.

FIG. 1 shows the pathway by which eicosapentaenoic acid (EPA) is synthesised within the human body from alpha-linolenic acid. FIG. 2 shows the other essential fatty acids which are related in structure to EPA. FIG. 3 shows the role of phospholipase $A_2$ in signal transduction in nerve cells. Various neurotransmitters, including dopamine, activate $PLA_2$ which leads to the formation of a lysophospholipid and a HUFA, both of which activate the cell. The activation is terminated by a fatty acid coenzyme A ligase (FACL), particularly FACL-4, which links coenzyme A to the HUFA, and then by an acyl coenzyme A transferase (ACT) which links the HUFA-coenzyme A to a lysophospholipid. In the process coenzyme A is liberated, a stable phospholipid molecule is reformed and the activation process is terminated.

Other EPA derivatives which could be used are the 2-substituted derivatives of EPA described by N Willumsen, I Vaagenes, H Holmsen and RK Berge (Biochim Biophys Acta 1369: 193–203, 1998). These have the advantage of having a longer duration of action because they are less readily oxidised.

EXAMPLE FORMULATIONS

In each of the following examples the product is at least 90% and preferably 95% or more pure. This is very important as other fatty acids will compete with the EPA for the binding sites and reduce its efficacy. In particular, fatty acids such as DHA, AA, DPA-n-3 will, individually, be present in concentrations of less than 5% and preferably less than 3%. The total aggregate of such competing compounds must be less than 10% and preferably less than 5%. This degree of purity is also valuable in minimising the volume of material which must be consumed each day, a major factor in helping compliance in psychiatric patients where lack of compliance is a serious problem.

1. Capsules made of hard or soft gelatin which contain 250 mg, 500 mg, or 1000 mg of ethyl-EPA, triglyceride EPA or other appropriate form of EPA.
2. Tablets containing 250 mg, 500 mg or 1000 mg lithium-EPA or hard gelatin capsules containing similar amounts.
3. Emulsions, solutions or dispersions in which the lithium-EPA, ethyl-EPA, triglyceride EPA or other appropriate form of EPA are prepared in a palatable liquid form for oral administration.
4. Suppositories or pessaries into which 100 mg to 5 g of one of the EPA compounds are formulated.
5. Intravenous solutions or emulsions containing from 10 mg to 500 mg/ml of one of the EPA compounds.
5–10. As examples 1–5, but using 2-substituted derivatives of EPA.
11–20. As in 1–10 but in which the EPA compound is formulated with the usual dose of any other drug used for the treatment of psychiatric or neurological disorders.
21–30. As in 1–10 but in which the EPA compound is formulated with clozapine.

What is claimed is:

1. A method of treating schizophrenia, a schizoaffective disorder, or a schizotypal disorder in a subject comprising administering to the subject a pharmaceutical preparation comprising EPA in an appropriately assimilable form, wherein of all the fatty acids present in the preparation at least 90% is in the form of EPA, and wherein less than 5% is in the form of docosahexaenoic acid (DHA), in conjunction with a drug which acts primarily on neurotransmitter metabolism or receptors.

2. The method of claim 1, wherein the drug is administered as a separate formulation.

3. The method of claim 1, wherein the drug is administered as part of the pharmaceutical preparation.

4. The method of claim 1, wherein the drug is clozapine.

5. The method of claim 1, wherein the drug is a typical or an atypical neuroleptic.

6. The method of claim 5, wherein the drug is chlorpromazine, haloperidol, risperidone, olanzapine, sertindole, ziprasidone, zotepine or amisulpiride.

7. The method of claim 1, wherein of all the fatty acids present in the preparation at least 95% is in the form of EPA.

8. The method of claim 1, wherein of all the fatty acids present in the preparation less than 3% is in the form of docosahexaenoic acid (DHA).

9. The method of claim 1, wherein among the other fatty acids present there are less than 5% of each of AA or DPA-n-3, individually.

10. The method of claim 1, wherein among the other fatty acids present there are less than 3% of each of AA or DPA-n-3, individually.

11. The method of claim 1, wherein the aggregate DHA, AA and/or DPA-n-3 content is less than 10% of the total fatty acids present.

12. The method of claim 1, wherein the aggregate DHA, AA and/or DPA-n-3 content is less than 5% of the total fatty acids present.

13. The method of claim 1, wherein the EPA is selected from the group consisting of: ethyl-EPA; lithium EPA; mono-, di- or triglyceride EPA; an ester or a salt of EPA; a free acid form of EPA; and an appropriate bioavailable EPA derivative which raises EPA levels in the subject.

14. A method of treating schizophrenia, a schizoaffective disorder, or a schizotypal disorder in a subject comprising administering to the subject a pharmaceutical preparation comprising EPA in an appropriately assimilable form, wherein of all the fatty acids present in the preparation at least 90% is in the form of EPA, and wherein less than 5% is in the form of docosahexaenoic acid (DHA).

15. The method of claim 14, wherein of all the fatty acids present in the preparation at least 95% is in the form of EPA.

16. The method of claim 14, wherein of all the fatty acids present in the preparation less than 3% is in the form of docosahexaenoic acid (DHA).

17. The method of claim 14, wherein among the other fatty acids present there are less than 5% of each of AA or DPA-n-3, individually.

18. The method of claim 14, wherein among the other fatty acids present there are less than 3% of each of AA or DPA-n-3, individually.

19. The method of claim 14, wherein the aggregate DHA, AA and/or DPA-n-3 content is less than 10% of the total fatty acids present.

20. The method of claim 14, wherein the aggregate DHA, AA and/or DPA-n-3 content is less than 5% of the total fatty acids present.

21. The method of claim 14, wherein the EPA is selected from the group consisting of: ethyl-EPA; lithium EPA; mono-, di- or triglyceride EPA; an ester or a salt of EPA; a free acid form of EPA; and an appropriate bioavailable EPA derivative which raises EPA levels in the subject.

* * * * *